United States Patent
Stepniewski et al.

(10) Patent No.: US 9,629,792 B2
(45) Date of Patent: Apr. 25, 2017

(54) MIXABLE MULTI-FUNCTIONAL PRODUCT AND PROCESS FOR KERATIN FIBERS

(71) Applicant: ELC Management LLC, Melville, NY (US)

(72) Inventors: George J. Stepniewski, Melville, NY (US); Paul H. Marotta, Farmingdale, NY (US); Katie Ann Frampton, West Babylon, NY (US); Christina Santa Maria, New York, NY (US); Nicole Packard, Huntington, NY (US)

(73) Assignee: ELC Management, LLC, Melville, NY (US)

( * ) Notice: Subject to any disclaimer, the term of this patent is extended or adjusted under 35 U.S.C. 154(b) by 222 days.

(21) Appl. No.: 14/271,556

(22) Filed: May 7, 2014

(65) Prior Publication Data

US 2015/0320672 A1    Nov. 12, 2015

(51) Int. Cl.
| | | |
|---|---|---|
| A61Q 1/10 | (2006.01) |
| A61K 8/891 | (2006.01) |
| A61K 8/31 | (2006.01) |
| A61K 8/81 | (2006.01) |
| A61K 8/49 | (2006.01) |
| A61K 8/26 | (2006.01) |
| A61K 8/06 | (2006.01) |
| A61Q 5/00 | (2006.01) |

(52) U.S. Cl.
CPC .............. *A61K 8/891* (2013.01); *A61K 8/064* (2013.01); *A61K 8/26* (2013.01); *A61K 8/31* (2013.01); *A61K 8/4973* (2013.01); *A61K 8/8111* (2013.01); *A61Q 1/10* (2013.01); *A61K 2800/43* (2013.01); *A61K 2800/884* (2013.01); *A61Q 5/00* (2013.01)

(58) Field of Classification Search
None
See application file for complete search history.

(56) References Cited

U.S. PATENT DOCUMENTS

| | | | |
|---|---|---|---|
| 2,676,182 A | 4/1954 | Daudt et al. | |
| 3,439,088 A | 4/1969 | Edman | |
| 3,818,105 A | 6/1974 | Coopersmith et al. | |
| 4,584,355 A | 4/1986 | Blizzard et al. | |
| 5,800,816 A | 9/1998 | Brieva et al. | |
| 6,967,024 B2 | 11/2005 | Scancarella et al. | |
| 2004/0161395 A1 | 8/2004 | Patil et al. | |
| 2005/0061349 A1* | 3/2005 | Patel | A45D 34/042 132/218 |
| 2007/0014744 A1 | 1/2007 | Swistowski et al. | |
| 2007/0193600 A1* | 8/2007 | Garofano | A45D 40/265 132/218 |
| 2011/0044924 A1 | 2/2011 | Verboom et al. | |
| 2011/0280820 A1* | 11/2011 | Bui | A61K 8/064 424/70.17 |
| 2012/0298128 A1 | 11/2012 | Hodgetts et al. | |
| 2012/0321367 A1* | 12/2012 | Bouix | A45D 40/262 401/1 |
| 2013/0045254 A1 | 2/2013 | Ting-Jenulis et al. | |
| 2013/0164241 A1* | 6/2013 | Foley | A61K 8/062 424/70.7 |
| 2013/0308823 A1* | 11/2013 | Smith | A45D 44/00 382/103 |

OTHER PUBLICATIONS

PCT International Search Report; International Application No. PCT/US2015/026990; Completion Date: Jun. 29, 2015; Mailing Date: Jun. 29, 2015.
PCT Written Opinion of the International Searching Authority; International Application No. PCT/US2015/026990; Completion Date: Jun. 29, 2105; Mailing Date: Jun. 29, 2015.
http://www.gnpd.com; Mintel; Liquid Lipstick; Record ID 1914518; Sephora; Kat Von D Foiled Love; Lip Colour Cosmetics—Lip Colour; USA; USA; Nov. 2012.
http://www.gnpd.com; Mintel; Overtime Lash Tint Mascara; Record ID 250084; Revlon Company; Colour Cosmetics; Eye Colour Cosmetics—Eye Lash; Netherlands; Jan. 2004.
http://www.gnpd.com; Mintel; Shimmer Eye Shadow Primer; Record ID: 2306753; Markwins Beauty Products; Wet n Wild Fergie CenterStage Collection Take on the Day; Colour Cosmetics; Face Colour Cosmetics—Primer; USA; Feb. 2014.
http://www.gnpd.com; Mintel; Waterproof Bold Volume Lifting Mascara; Record ID: 1320468; Estee Lauder; Colour Cosmetics; Eye Colour Cosmetics—Eye Lash; Canada; May 2010.
PCT Written Opinion of the International Searching Authority; International Application No. PCT/US2015/026990; Completion Date: Jun. 29, 2015; Mailing Date: Jun. 29, 2015.

* cited by examiner

*Primary Examiner* — Tracy Vivlemore
*Assistant Examiner* — Monica Shin
(74) *Attorney, Agent, or Firm* — Julie Blackburn

(57) ABSTRACT

A mixable multi-functional composition for application to keratin fibers such as hair, lashes or brows comprising at least one volatile solvent, at least one siloxane resin, at least one montmorillonite mineral, optionally at least one non-volatile oil, and optionally at least one wax; and a method for coloring keratin fibers comprising the steps of sequentially applying to the fibers, in any order, at least one mixable composition and at least one pigmented composition, wherein upon application the mixable composition mixes and combines with the pigmented composition in the wet state to form a final mixed composition that upon drying forms a compatible and homogeneous film.

10 Claims, No Drawings

MIXABLE MULTI-FUNCTIONAL PRODUCT AND PROCESS FOR KERATIN FIBERS

TECHNICAL FIELD

The invention is in the field of products for application to eyelashes and eyebrows which have multiple benefits and functions.

BACKGROUND OF THE INVENTION

Foundation primers are well known in the cosmetics industry. A foundation primer is a base composition applied to the face prior to application of foundation. Primers may correct color, correct the appearance of unevenly pigmented skin, and create a base for application of foundation to provide a smooth perfected finish to facial skin. Foundation primers are typically applied, allowed to dry, and followed by application of foundation. Lash primers are also known, most often in mascaras sold in two pack form. These types of mascaras typically contain a primer composition for application to the lashes first, and a second colored mascara composition. In most cases the primer compositions are white or grayish in color to distinguish the primer from the actual mascara product, and the primer is allowed to dry before the mascara is applied.

Women who use beauty products most often lead very busy lives. Often they do not have the time or inclination to carefully follow instructions to maximize the effectiveness of their beauty products. For example, with two pack lash products, women simply apply them sequentially without paying much attention to amount or timing. Moreover, the products often contain only very generic instructions that advise the user to apply products sequentially but with no additional guidance on timing or volume. Leaving the specific details to the consumer does not always provide the optimal result. One other complication is that in typical two pack products the primer compositions are white or gray in color. When the primer and mascara coats are sequentially applied, the primer often mutes the color intensity of the final product on the lashes.

Accordingly, it is an object of the invention to provide a composition for application to keratin fibers such as hair, lashes or brows that may serve multiple functions including color lashes, a primer composition for application to lashes or brows to improve the benefits of a subsequently applied mascara or brow color, or a lash sealant that will make lashes to which mascara has been applied water proof or water resistant. It is also an object of the invention to provide a composition that is mixable with other product compositions in the wet state such that when the composition of the invention is applied sequentially with other products with no intervening dry time the two compositions are mixable, and when mixed, provide significantly improved end benefits without sacrificing color intensity.

SUMMARY OF THE INVENTION

The invention is directed to a mixable multi-functional composition for application to keratin fibers such as hair, lashes or brows comprising at least one volatile solvent, at least one siloxane resin, at least one montmorillonite mineral, optionally at least one non-volatile oil, and at least one wax.

The invention is also directed to a method for coloring keratin fibers comprising the steps of sequentially applying to the fibers, in any order, at least one mixable composition and at least one pigmented composition, wherein upon application the mixable composition mixes and combines with the pigmented composition in the wet state to form a final mixed composition that upon drying forms a compatible and homogeneous film.

More specifically, one embodiment in the method of the invention comprises the steps of:

(a) applying to keratin fibers a mixable composition comprising preferably comprising at least one volatile solvent, at least one siloxane resin, at least one montmorillonite mineral, optionally at least one non-volatile oil, and optionally at least one wax; and (b) thereafter, and prior to air drying of composition (a), application of a second pigmented composition (b) said composition being combined with the composition of (a) in the application process to form a mixed composition that is then allowed to air dry on the keratin fibers to provide a homogeneous film.

Another embodiment of the invention is directed to a method for coloring keratin fibers comprising the steps of:

(a) applying a pigmented lash or brow color composition to the keratin fibers, (b) immediately thereafter, and prior to air drying of the (a) composition, application of a second mixable composition comprising, preferably, at least one volatile solvent, at least one siloxane resin, at least one montmorillonite mineral, and optionally at least one non-volatile oil, and optionally at least one wax wherein composition (b) is combined and mixed with composition (a) during the application process; and (c) allowing the mixed composition to air dry on the keratin fibers to form a homogeneous film.

DETAILED DESCRIPTION

All percentages mentioned herein are percentages by weight unless otherwise indicated.

All documents mentioned herein are incorporated by reference in their entirety.

The term "compatible" means, with respect to the combined pigmented composition and the mixable composition, that the two compositions are compatible and will not separate or otherwise be unstable due to the mixture of the two compositions.

The term "homogeneous" means, with respect to the combined mixable and pigmented compositions that the combined compositions have structural integrity.

The term "oil" means a pourable liquid at room temperature, e.g. 25° C.

The term "non-volatile" means that the oil has a vapor pressure of less than 20 mm. of mercury at 20° C.

The term "volatile" means that the oil has a vapor pressure of more than 20 mm. of mercury at 20° C.

The term "mixable" means with respect to the composition of the invention that when in the wet state it will readily combine or mix with any other product when in the wet state to form a homogeneous composition that is internally compatible and is also compatible with such composition both in the wet state and after the mixed composition has dried.

The term "keratin fibers" means hair, eyelashes, or eyebrows.

The mixable composition has ingredients including but not limited to those set forth herein.

Volatile Solvents

Suitable volatile solvents generally have a viscosity ranging from about 0.5 to 5 centistokes (cst) at 25° C. and include linear silicones, cyclic silicones, branched silicones, paraffinic hydrocarbons, or mixtures thereof. The volatile solvent may be present in amounts ranging from about 0.1 to 95%, preferably 0.5 to 85%, more preferably from about 1 to 80%.

Cyclic silicones are one type of volatile silicone that may be used in the composition. Such silicones have the general formula:

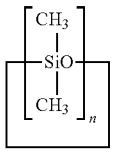

where n=3-6, preferably 4, 5, or 6.

Also suitable are linear volatile silicones, for example, those having the general formula:

$$(CH_3)_3Si-O-[Si(CH_3)_2-O]_n-Si(CH_3)_3$$

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 cst), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

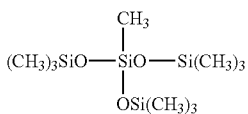

Methyl trimethicone may be purchased from Shin-Etsu Silicones under the tradename TMF-1.5, having a viscosity of 1.5 centistokes at 25° C.

Also suitable as the volatile solvents are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

The volatile solvent is preferably present in the mixable composition of the invention in amounts ranging from about 1 to 80%, preferably 5-60%, more preferably from about 10-50%. Most preferred is where the volatile solvent comprises a mixture of volatile paraffinic hydrocarbons and volatile silicone in a ratio of about 5-25 parts of volatile paraffinic hydrocarbon (e.g. isododecane, isohexadecane) to 1 part of volatile silicone (e.g. trisiloxane).

The Crosslinked Silicone Film Former

The crosslinked silicone film former used in the method and compositions of the invention comprises the reaction product of a siloxane resin and a diorganosiloxane. Preferably, the amount of silicone copolymer in the compositions ranges from about 0.001 to 50%, preferably about 0.01-40%, more preferably about 0.1-35% by weight of the total composition. This type of siloxane resin exhibits a plasticity that facilitates mixing, enables formulation with lesser amounts of oily plasticizers (which in turn reduce wear and adhesion).

Preferably, the siloxane resin is comprised of T or Q units, which may have M units and D units; and the diorganosiloxane is comprised of M and D units.

The term "M unit" means a monofunctional unit, which is a siloxy unit that contains one silicon atom bonded to one oxygen atom, with the remaining three substituents on the silicon atom being other than oxygen. In particular, in a monofunctional siloxy unit, the oxygen atom present is shared by 2 silicon atoms when the monofunctional unit is polymerized with one or more of the other units. In silicone nomenclature used by those skilled in the art, a monofunctional siloxy unit is designated by the letter "M", and means a unit having the general formula:

$$R_1R_2R_3-Si-O_{1/2}$$

wherein $R_1$, $R_2$, and $R_3$ are each independently $C_{1-30}$, preferably $C_{1-10}$, more preferably $C_{1-4}$ straight or branched chain alkyl, or $C_{1-30}$, preferably $C_{1-10}$, more preferably $C_{1-4}$alkoxy, which may be substituted with phenyl or one or more hydroxyl groups; phenyl; carboxylic esters; or hydrogen. The $SiO_{1/2}$ designation means that the oxygen atom in the monofunctional unit is bonded to, or shared, with another silicon atom when the monofunctional unit is polymerized with one or more of the other types of units. For example, when $R_1$, $R_2$, and $R_3$ are methyl the resulting monofunctional unit is of the formula I:

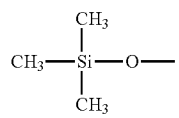

When this monofunctional unit is polymerized with one or more of the other units the oxygen atom will be shared by another silicon atom, i.e. the silicon atom in the monofunctional unit is bonded to 1/2 of this oxygen atom.

The term "difunctional siloxy unit" is generally designated by the letter "D" in standard silicone nomenclature. If the D unit is substituted with substituents other than methyl the "D" designation is sometimes used, which indicates a substituent other than methyl. For purposes of this disclosure, a "D" unit has the general formula:

$$R_1R_2-Si-O_{2/2}$$

wherein $R_1$ and $R_2$ are defined as above. The $SiO_{2/2}$ designation means that the silicon atom in the difunctional unit is bonded to two oxygen atoms when the unit is polymerized with one or more of the other units. For example, when $R_1$ and $R_2$ are methyl the resulting difunctional unit is of the Formula II:

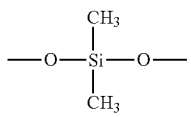

When this difunctional unit is polymerized with one or more of the other units the silicon atom will be bonded to two oxygen atoms, i.e. will share two one-halves of an oxygen atom.

The term "trifunctional siloxy unit" is generally designated by the letter "T" in standard silicone nomenclature. A "T" unit has the general formula:

$R_1SiO_{3/2}$ wherein $R_1$ is as defined above. The $SiO_{3/2}$ designation means that the silicon atom is bonded to three oxygen atoms when the unit is copolymerized with one or more of the other units. For example when R1 is methyl the resulting trifunctional unit is of Formula III:

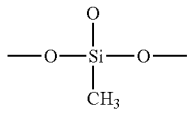

When this trifunctional unit is polymerized with one or more of the other units, the silicon atom shares three oxygen atoms with other silicon atoms, i.e. will share three halves of an oxygen atom.

The term "tetrafunctional siloxy unit" is generally designated by the letter "Q" in standard silicone nomenclature. A "Q" unit has the general formula:

$Si—O_{4/2}$

The $SiO_{4/2}$ designation means that the silicon shares four oxygen atoms (i.e. four halves) with other silicon atoms when the tetrafunctional unit is polymerized with one or more of the other units. The $SiO_{4/2}$ unit is best depicted as follows:

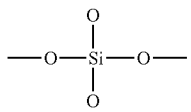

The silicone polymer used in the composition are made according to processes well known in the art. In general siloxane polymers are obtained by hydrolysis of silane monomers, preferably chlorosilanes. The chlorosilanes are hydrolyzed to silanols and then condensed to form siloxanes. For example, Q units are often made by hydrolyzing tetrachlorosilanes in aqueous or aqueous/alcoholic media to form the following:

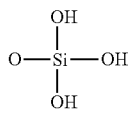

The above hydroxy substituted silane is then condensed or polymerized with other types of silanol substituted units, in this units including diorganosiloxane units, such as:

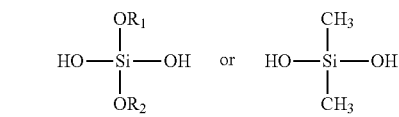

wherein $R_1$ and $R_2$ are as defined above.

Because the hydrolysis and condensation may take place in aqueous or aqueous/alcoholic media wherein the alcohols are preferably lower alkanols such as ethanol, propanol, or isopropanol, the units may have residual hydroxyl or alkoxy functionality. Preferably, the polymers are made by hydrolysis and condensation in aqueous/alcoholic media, which provides resins that have residual silanol and alkoxy functionality. In the case where the alcohol is ethanol, the result is a resin that has residual hydroxy or ethoxy functionality on the siloxane polymer. The silicone film forming polymers used in the compositions of the invention are generally made in accordance with the methods set forth in Silicon Compounds (Silicones), Bruce B. Hardman, Arnold Torkelson, General Electric Company, Kirk-Othmer Encyclopedia of Chemical Technology, Volume 20, Third Edition, pages 922-962, 1982, which is hereby incorporated by reference in its entirety.

If desired, the hydroxy functional groups on the molecule may be further reacted to form alkoxy groups, alkyl groups, halogens, which may be substituted with one or more substituents such as hydroxyl, and so on.

Most preferred is where the siloxane copolymer is obtained by reacting a diorganosiloxane having terminal hydroxyl groups with a siloxane resin having hydroxyl groups by combining the reactants in the presence of heat and ammonia, as set forth in U.S. Pat. No. 4,584,355, which is hereby incorporated by reference in its entirety.

Particularly preferred are silicone copolymers manufactured by Dow Corning which are sold under the series 4100, 4200, 4300, 4400, 4500 or 4600. Most preferred are the Dow Corning silicone copolymers sold under the DC7-4405 trade name having the CTFA name dimethicone silylate which is referred to by the chemical name trimethylated silica treated with dimethicone.

Non-Volatile Oils

A variety of nonvolatile oils are also suitable for use in the compositions of the invention. If present, suggested ranges are from about 0.1 to 60%, preferably from about 2.5 to 40%, more preferably from about 1 to 15%. The nonvolatile oils generally have a viscosity of greater than about 5 to 10 centistokes at 25° C., and may range in viscosity up to about 1,000,000 centipoise at 25° C. Examples of nonvolatile oils include, but are not limited to those further described herein.

1. Esters

Suitable esters are mono-, di-, and triesters. The composition may comprise one or more esters selected from the group, or mixtures thereof.

(a) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(b). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisopropyle adipate, diisosteatyl dimer dilinoleate, diisostearyl fumarate, diisostearyl malate, dioctyl malate, and so on.

(c). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety. Particularly preferred esters include esters of sorbitan, in particular, sorbitan olivate, sorbitan tristearate, sorbitan stearate, and the like.

Particularly preferred for use in the mixable composition of the invention are mono-, di-, tri-, or tetraesters of sorbitan where one or more of the hydroxyl groups of sorbitan are esterified with C6-30, preferably C10-22, more preferably C8-20 saturated or unsaturated fatty acids such as stearic, cetylstearic, behenic, oleic acid, linoleic acid, and so on. Particularly preferred are sorbitan esters where one or more, preferably three, hydroxyl groups of sorbitan are esterified with stearic acid and sorbitan esterified with fatty acids from olive oil (e.g. sorbitan olivate), Most preferred are sorbitan tristearate and sorbitan olivate.

2. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons. Particularly preferred are isoparaffins which may be hydrogenated. Particularly preferred are hydrogenated polyisobutene, polyisobutene, polybutene, polydecene, and the like.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

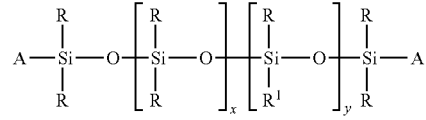

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

Waxes

The preferred compositions of the invention may also contain waxes, which may be animal, vegetable, or mineral waxes, Preferably such waxes will have a higher melting point such as from about 50 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, *acacia*, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof; such as hydroxystearic acids (for example 12-hydroxy stearic acid), tristearin, tribehenin, and so on. Particularly preferred are microcrystalline wax, trihydroxystearin, polyethylene, and the like.

Montmorillonite Minerals

Preferred compositions used in the method of the invention contain montmorillonite minerals. Suggested ranges are from about 0.5 to 25%, preferably from about 1 to 15%, more preferably from about 1.5 to 5. The montmorillonite mineral may be quaternized, which means that it has been reacted with quaternary ammonium compounds, such as Quaternium-18 or distearyl dimonium chloride and the like. The montmorillonite mineral is generally in the form of platelets or sheets that may or may not be interconnected. If desired the montmorillonite mineral may be sheared to form nanoparticles or nanoplatelets, or sheets, of very small thickness. In such case the nanoplatelets have thicknesses ranging from about 0.5 to 5 nanometers (0.0005 to 0.005 microns). Preferably, the top surface area of the nanoplatelet ranges from about 20 to 2000 nanometers (0.02 to 2 microns).

Suitable montmorillonite minerals include synthetic or natural metal silicates such sodium, potassium, magnesium, aluminum, lithium, zinc, iron, calcium, or beryllium silicates or mixtures thereof. Natural metal silicates are also known as "hectorites" or "bentonites".

Particularly preferred for use in the mixable composition of the invention are montmorillonite minerals dispersed in volatile or non-volatile, preferably volatile solvents. The dispersion promotes slower evaporation of the solvent which extends the dry time (or "play time") of the mixable composition to permit mixing with the pigmented composition. More preferred is where the montmorillonite minerals are quaternized montmorillonite minerals and in the form of a dispersion comprising from about 5-35% quaternized montmorillonite mineral such as Quaternium-90 bentoniate, and from about 40-95% of oil, preferably volatile oil such as volatile paraffinic hydrocarbons or volatile silicones, and optionally from about 1-10% of an alkylene carbonate (e.g. propylene carbonate) or similar stabilizing agents such as triethyl citrate.

Particularly preferred for use in the compositions of the invention are quaternized montmorillonite minerals, more specifically Quaternium-90 bentonite which may be purchased in the form of a dispersion containing 2.5% propylene carbonate, 17.5 Quaternium-90 bentonite, and 80% isododecane sold under the tradename Distinctive Gel ID by D.C. Incorporated, Plainfield, N.J., Particulate Materials The mixable composition of the invention may, if desired, contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

A. Powders

The particulate matter may be colored or non-colored (for example white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

B. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

The composition may contain a variety of other ingredients including but not limited to preservatives, humectants, anti-foam agents, and so on.

In general, the mixable composition of the invention has a longer dry time than standard mascaras or primers. This is true even in spite of its volatile content and is due to a number of factors. First, the preferred water in oil emulsion form means that the water is the internal dispersed phase in the continuous oil phase. Water is the most volatile ingredient of all, and the fact that the water is in essence "sequestered" means that it evaporates much more slowly from the lashes or brows when applied. A second contributing factor is that when the monmorillonite mineral is supplied to the composition in the form of a gel comprising a dispersion of from about 5-40% quaternized montmorillonite mineral, 40-95% volatile solvent, and optionally 0.5-15% alkylene carbonate the evaporation rate of the volatile solvent is slowed, thus further contributing to the extended dry time of the mixable composition. More specifically, a preferred monmorillonite mineral composition comprises from about 0.5-15% propylene carbonate, 5-40% Quaternium-90 bentonite, and 40-95% isododecane. Most preferred is where the montmorillonite mineral is in a dispersion of 2.5% propylene carbonate, 17.5 Quaternium-90 bentonite, and 80% isododecane sold under the tradename Distinctive Gel ID.

Most preferred is where the mixable composition is an emulsion, specifically a water in oil emulsion comprising from about 0.1-30% water phase and from about 60-99.9% oil phase. More specific examples of different embodiments of the mixable composition are:

A mixable composition comprising 0.5 to 85% of a volatile solvent which is isododecane, isohexadecane or trisiloxane; 0.01-35% of dimethicone silylate; 1-15% of a non-volatile oil which is a sorbitan ester, paraffinic hydrocarbon, or mixtures thereof; and 0.1-20% of a quaternized montmorillonite mineral; and 0.5-10% wax.

A mixable composition comprising 0.5 to 80% of a volatile solvent which is a mixture of 5-25 parts of isododecane to 1 part of trisiloxane; 0.01-3% of dimethicone silylate, 1-15% of a non-volatile oil comprising a mixture of sorbitan tristearate, sorbitan olivate, and polyisobutene; 0.1-10% of Quaternium-90 bentonite; and 0.5-10% wax.

A mixable composition in the water in oil emulsion form comprising 0.5-80% of a mixture of a volatile solvent comprising 5-25 parts of volatile paraffinic hydrocarbon to 1 part of volatile silicone; 0.1-12% of a crosslinked silicone polymer comprising a diorganosiloxane having terminal hydroxyl groups with a siloxane resin hydroxyl groups by combining reactants in the presence of heat and ammonia; from 1-15% of a non-volatile oil which is an ester of sorbitan and a C6-30 carboxylic acid and a paraffinic hydrocarbon; 0.1-10% quaternized montmorillonite mineral; and 0.5-10% wax.

A mixable composition 0.5-80% of a volatile solvent comprising isododecane; 0.1-12% dimethicone silylate; 1-15% of a non-volatile oil; 0.1-10% of Quaternium-90 bentonite.

A mixable water in oil emulsion composition comprising 0.5-80% of a mixture of isododecane and trisiloxane; 0.1-12% dimethicone silylate; 1-15% of a mixture of sorbitan tristearate, sorbitan olivate, and polyisobutene; 0.1-10% Quaternium-90 bentonite, and 2-40% water.

A mixable emulsion composition comprising 0.5-80% of a mixture of volatile paraffinic hydrocarbon and volatile silicone; 0.1-12% dimethicone silylate; 1-15% of one or more esters of sorbitan and a C6-30 carboxylic acid; 0.1-10% of a quaternized montmorillonite mineral; and 0.1-15% pigment, and 5-35% water.

The Methods of the Invention

The invention is also directed to a method for coloring keratin fibers comprising the steps of sequentially applying to the fibers, in any order, at least one mixable composition and at least one pigmented composition, wherein upon application the mixable composition mixes and combines with the pigmented composition in the wet state to form a final mixed composition that upon drying forms a compatible and homogeneous film. The sequentially applied compositions are applied wet on wet, which means the first and second compositions are applied on top of each other before they have dried. This generally means that no more than 10-120 seconds, preferably 20-100 seconds, more preferably 30-95 seconds elapses between application of the first and second sequentially applied compositions.

One more specific embodiment of the invention is a method for coloring keratin fibers comprising the steps of:

(a) applying to the keratin fibers the mixable composition as described herein which preferably comprises at least one volatile solvent, at least one siloxane resin, at least one montmorillonite mineral, and optionally at least one non-volatile oil, and at least one wax; and (b) immediately thereafter, and prior to air drying of composition (a) application of a second pigmented composition (b) said composition being mixed with the composition of (a) upon application to form a mixed composition that is then allowed to air dry.

More specifically, the (a) composition is applied to the keratin fibers with a twisted metal wire brush or similar applicator with the product (a) loaded on the brush using from 10-60 strokes of the applicator against the fibers depending on the effect desired. Most preferred is where about 0.05 to 0.30 grams, preferably from about 0.08 to 0.20, most preferably from about 0.09 to 0.15 grams of the composition of (a) is applied to keratin fibers, specifically eyelashes, using from 10-60, preferably from about 15-40, more preferably from about 18-25 strokes of the applicator without inserting the applicator into the product container to recharge when applying to one lash. More specifically, the (a) composition is applied to the lashes of one eye without recharging the brush using the amounts and the strokes specified. Then, the applicator is recharged with the (a) composition and is used to apply the composition it to the lashes of the second eye with the load and the strokes mentioned with respect to the lashes of the first eye. Because composition (a) has a longer drying time than other similar primers or mascaras, if the second composition (b) is then applied to the lashes of each eye individually following the same sequence, composition (a), due to its longer drying time, will not have dried by the time composition (b) is applied. This enables mixing of composition (b) with the undried composition (a) during the application process. This in turn improves properties of the final applied compositions such as flaking, smudging, wear, and adhesion.

The pigmented lash or brow composition referred to herein is generally a composition in the emulsion form, preferably an oil-in-water emulsion. The composition generally contains from about 1-80% water, 0.1-25% film forming polymer, from about 0.1-20% oil, and from about 0.1-20% pigments, with the oil and pigments as referred to herein with respect to the mixable composition. However, the mixable composition of the invention may be suitable for use with a wide variety of lash or brow compositions, including those that are anhydrous.

In the most preferred embodiment the pigmented lash or brow composition is an oil-in-water emulsion and the mixable composition is a water-in-oil emulsion. When the mixable composition is applied wet on wet with the pigmented lash composition that resulting mixture may form a multiple emulsion, that is, a water-in-oil-in-water or an oil-in-water-in-oil emulsion. Similarly if the pigmented lash composition is anhydrous, when it is combined with the mixable composition the resulting mixture is most likely a water-in-oil emulsion.

The method of invention provides improvement in lash coating in particular where the percentage improvement with application of the mixable composition and the lash color composition sequentially with no air drying between applications is as follows:

|  | After immediate application | 16 hours after application | 24 hours after application |
|---|---|---|---|
| % increase in lash length | 35-75% | 28-60% | 18-40% |
| % increase in lash volume | 120-150% | 110-140% | 65-100% |
| % increase in lash curl | 10-40% | 15-50% | 10-35% |
| % lash separation | 15-25% | 13-20% | 10-15% |
| % lash thickness | 30-50% | 35-45% | 18-40% |
| % lash spiking | 14-30% | 14-20% | 20-30% |
| % lash clumping* | 13-20% | 13-20% | 13-20% |
| % lash flaking* | 10-20% | 12-16% | 12-15% |
| % lash smudging* | 17-30% | 17-25% | 18-22% |
| % lash wear | 15-25% | 15-20% | 12-18% |

*reduced % is better

In a second embodiment of the invention, the mixable composition may be applied according to the following process:

The invention is also directed to a method for coloring keratin fibers comprising the steps of:

(a) applying a pigmented composition to the keratin fibers, (b) immediately thereafter, and prior to air drying of the (a) composition, application of a second mixable composition comprising at least comprising at least one volatile solvent, at least one siloxane resin, at least one montmorillonite mineral, at least one non-volatile oil, and at least one wax wherein composition (b) is combined and mixed with composition (a) during the application process; and (c) allowing the mixed composition to air dry on the keratin fibers.

In this case the mixable composition is applied, preferably, to the lashes or brows after the application of color, in particular, after the application of mascara. The mixable composition provides an excellent sealant that increases the wear of the mascara on the lashes.

As mentioned above with respect to the first embodiment, in general the pigmented lash or brow color composition is applied first to the lashes using an applicator where from about 0.05 to 0.45, preferably from about 0.1 to 0.35, most preferably from about 0.15 to 0.30 grams of product is applied to the lashes of one eye using from about 20-60, preferably about 25-55, more preferably from about 30-50 strokes without recharging the brush between the strokes. The pigmented composition is similarly applied to the lashes of the second eye. Then, preferably immediately thereafter without permitting drying of the pigmented lash composition, the mixable composition is applied to the lashes of the first treated eye by charging the applicator with from about 0.05 to 0.40, preferably from about 0.08 to 0.30, more preferably from about 0.1 to 0.20 grams of mixable composition applied with from about 10-50, preferably from about 12-40, most preferably from about 15-25 strokes, Preferred is where the applicator is not recharged with mixable composition between strokes. The applicator is then recharged and the same load of the mixable composition is then applied to the lashes of the second eye using the same number of strokes and without recharging the applicator between strokes. Upon application, the mixable composition will combine with the first applied pigmented lash composition to form a compatible and homogeneous mixture that dries to form a sealant on the lashes that will increase the wear and adhesion of the first applied lash or brow composition.

Most preferred is where the pigmented lash composition is an oil in water emulsion, with a dry time ranging from about 5 to 20 minutes and wherein the mixable composition has a dry time ranging from about 20.1 to 40 minutes when the dry time is measured with a Gardner Circular Drying Time Recorder, More specifically, a 2 mil thick film of the test composition is spread on 0.15 mm plastic sheet. The Drying Time Recorder is placed on the sheet and the teflon stylus into position over the film. The switch is turned on. The stylus containing a 12 gram load, is moved in a 360° arc at a fixed speed over the film. The shaft arm with the teflon ball subscriber produces a 2 inch diameter circular path. Drying time is observed and recorded as the ball penetrates the film and produces a circular groove over the area. When the drying path is no longer visible the switch is turned off. The dry time record can be converted into minutes or hours. The test sheet is evaluated using the Time Template provided with the Recorder to determine the dry time.

The invention will be further described in connection with the following Examples which are set forth for the purposes of illustration only.

Example 1

A mixable multi-functional lash composition in water in oil emulsion form was prepared as follows:

| Ingredient | % by weight |
|---|---|
| Isododecane | QS100 |
| Water | 21.30 |
| Dimethicone silylate | 8.80 |
| Sorbitan olivate | 7.70 |
| Quaternium-90 bentonite | 4.12 |
| Trisiloxane | 3.55 |
| Sorbitan tristearate | 2.20 |
| Silica silylate | 2.00 |
| Polyisobutene | 1.85 |
| Carnauba wax | 1.00 |
| Diisopropyl adipate | 1.00 |
| Trihydroxystearin | 1.00 |
| Iron oxides | 0.98 |
| Phenoxyethanol | 0.64 |
| Propylene carbonate | 0.60 |
| Microcrystalline wax | 0.50 |
| Cholesterol | 0.25 |
| Caprylyl glycol | 0.22 |
| Magnesium salicylate | 0.20 |
| Hexylene glycol | 0.04 |
| Panthenol | 0.03 |
| Trimethylsiloxysilicate | 0.03 |
| Pantethine | 0.02 |
| Methicone | 0.02 |

The composition was prepared by separately combining the oil and water phase ingredients, then mixing well to emulsify.

Example 2

The composition of Example 1 was applied to panelist lashes from a mascara container having an opening wiper width of 0.136 inch using a twisted metal wire brush on a rod having a length of 0.141 inch. The brush was loaded with the Example 1 formula by inserting into the container and withdrawing to load the brush. The product was applied with 40 strokes of the brush. Immediately, and 10 hours, after application the lashes to which the composition was applied, Photographs of the lashes were taken and trained advisors analyzed the images of lashes for length, volume, and curl compared with baseline. In addition, trained evaluators evaluated the lashes to which the composition had been applied for various parameters including separation, thickness, spiking, etc.

Results of image analysis of treated lashes over baseline is shown in the table below:

| Parameter | % increase compared to baseline when measured immediately after application | % increase compared to baseline when measured 10 hours after application |
|---|---|---|
| Lash length | 20% | 17% |
| Lash volume | 72% | 65% |
| Lash curl | 14% | 10% |

Results of trained expert panel evaluation of treated lashes over baseline is shown in the table below:

| Parameter | % increase over baseline immediately after application | % increase over baseline 10 hours after application |
|---|---|---|
| Lash separation | 14% | 10% |
| Lash thickness | 18% | 15% |
| Lash spiking | 14% | 16% |
| Lash clumping | 4% | 4% |
| Lash flaking | — | 7% |
| Lash smudging | — | 8% |
| Wear on lashes | — | 13% |
| Overall look | 16% | 12% |
| # strokes | 40 | |

Example 3

The composition of Example 1 was tested alongside a commercial mascara product having the following ingredients as set forth on the label:
WATER\AQUA\EAU [ ] ACRYLATES/ETHYLHEXYL ACRYLATE COPOLYMER [ ] COPERNICIA CERIFERA (CARNAUBA) WAX\CERA CARNAUBA\CIRE DE CARNAUBA [ ] GLYCERYL STEARATE [ ] POLYISOBUTENE [ ] SYNTHETIC BEESWAX [ ] STEARIC ACID [ ] ACRYLATES COPOLYMER [ ] KAOLIN [ ] TALC [ ] TROMETHAMINE [ ] PANTHENOL [ ] PANTETHINE [ ] CHOLESTEROL [ ] BUTYLENE GLYCOL [ ] 1,2-HEXANEDIOL [ ] LINOLEIC ACID [ ] HYDROGENATED LECITHIN [ ] STEARETH-2 [ ] LAURETH-21 [ ] AMMONIUM ACRYLATES COPOLYMER [ ] LAUROYL LYSINE [ ] PVP/HEXADECENE COPOLYMER [ ] *ACACIA* SENEGAL GUM [ ] STEARETH-21 [ ] PHYTANTRIOL [ ] PHENETHYL ALCOHOL [ ] POLYETHYLENE TEREPHTHALATE [ ] LAURETH-20 [ ] ISOSTEARIC ACID [ ] HYDROXYETHYLCELLULOSE [ ] TOCOPHERYL ACETATE [ ] CAPRYLYL GLYCOL [ ] SIMETHICONE [ ] TETRAHEXYLDECYL ASCORBATE PTFE [ ] SILICA [ ] DISODIUM EDTA [ ] CHLOROXYLENOL [ ] POTASSIUM SORBATE [ ] SODIUM DEHYDROACETATE [ ] PHENOXYETHANOL [ ] [+/−IRON OXIDES (CI 77491, CI 77492, CI 77499) [ ] MICA [ ] MANGANESE VIOLET (CI 77742) [ ] CHROMIUM OXIDE GREENS (CI 77288) [ ] TITANIUM DIOXIDE (CI 77891) [ ] FERRIC FERROCYANIDE (CI 77510) [ ] CHROMIUM HYDROXIDE GREEN (CI 77289) [ ] CARMINE (CI 75470) [ ] BISMUTH OXYCHLORIDE (CI 77163) [ ] ULTRAMARINES (CI 77007)]<ILN38474>

The Example 1 composition was applied using the same brush, wiper, and rod as set forth in Example 2. The Example 3 composition was applied using a twisted metal wire brush from a mascara container having a wiper diameter of 0.145 to 0.149 inch and a rod length of 0.140. Twenty strokes of the Example 1 composition was applied followed by 40 strokes of the Example 3 composition. The brush was recharged when moving to apply to the second eye. The results were subjected to image analysis and observation by a trained evaluator.

Results of image analysis of treated lashes over baseline is shown in the table below:

| Parameter | % increase compared to baseline when measured immediately after application | % increase compared to baseline when measured 16 hours after application | % increase when measured 24 hours after application |
|---|---|---|---|
| Lash length | 33% | 25% | 16% |
| Lash volume | 118% | 105% | 53% |
| Lash curl | 17% | 13% | 9% |

Results of trained expert panel evaluation of treated lashes over baseline is shown in the table below:

| Parameter | % increase over baseline immediately after application | % increase over baseline 16 hours after application | % increase over baseline 24 hours after application |
|---|---|---|---|
| Lash separation | 18% | 14% | 11% |
| Lash thickness | 29% | 27% | 21% |
| Lash spiking | 18% | 22% | 25% |
| Lash clumping | 13% | 13% | 13% |
| Lash flaking | — | 17% | 23% |
| Lash smudging | — | 18% | 25% |
| Wear on lashes | — | 19% | 30% |
| Overall look | 30% | 21% | 16% |
| # strokes | | 40 | |

Example 4

The composition of the invention as set forth in Example 1 was applied along with the commercial mascara product set forth in Example 3 as set forth in Example 3. In particular, the composition of Example 1 was used as primer and 20 strokes of the composition of Example 1 was applied to the lashes immediately followed by 40 strokes of the commercial mascara product of Example 3, with no dry time allowed between the applications.

In a second test, the Example 3 commercial product was applied to the lashes with 40 strokes followed by 20 strokes of the composition of Example 1 from the same containers and using the same applicators as set forth in Example 3. The results are set forth in the table below.

| | E1[1] | E3[2] | | | E1 + E3[3] | | | E3 + E1[4] | | |
|---|---|---|---|---|---|---|---|---|---|---|---|
| | | | | | Time in hours | | | | | | |
| | 0 | 10 | 0 | 16 | 24 | 0 | 16 | 24 | 0 | 16 | 24 |
| Lash length % inc. | 20 | 17 | 33 | 25 | 16 | 38 | 31 | 20 | 37 | 32 | 21 |
| Lash volume % inc. | 72 | 65 | 118 | 105 | 53 | 127 | 117 | 74 | 130 | 115 | 72 |
| Lash Curl % inc. | 14 | 10 | 17 | 13 | 9 | 18 | 13 | 10 | 18 | 14 | 11 |
| Lash separation % | 14 | 10 | 18 | 14 | 11 | 18 | 15 | 11 | 19 | 16 | 11 |
| Lash thickness % | 18 | 15 | 29 | 27 | 21 | 33 | 29 | 24 | 33 | 27 | 22 |
| Lash spiking % | 14 | 16 | 18 | 22 | 25 | 20 | 23 | 24 | 21 | 21 | 23 |
| Lash clumping % | 4 | 4 | 13 | 13 | 12 | 14 | 14 | 14 | 15 | 15 | 14 |
| Lash flaking % | — | 7 | — | 17 | 23 | — | 15 | 19 | — | 13 | 17 |
| Lash smudging % | — | 8 | — | 18 | 25 | — | 15 | 18 | — | 17 | 18 |
| Lash wear % | — | 13 | — | 19 | 30 | — | 17 | 25 | — | 15 | 26 |
| Overall look % | — | 13 | 30 | 21 | 16 | 32 | 26 | 20 | 33 | 25 | 19 |

[1]Composition of Example 1 applied to lashes, 20 strokes
[2]Composition of Example 3 applied to lashes, 40 strokes
[3]Composition of Example 1 applied to lashes, 20 strokes, followed immediately by Example 3 commercial product, 40 strokes
[4]Composition of Example 3 applied to lashes, 40 strokes, followed immediately by Example 1 commercial product, 20 strokes The above results show that when the Example 1 mixable composition is applied with the commercial product of Example 3 the desired benefits such as curl, length, volume, separation, and so on are significantly more sustainable over time. The mixed composition wears better and shows improved lash curling, length and other parameters when measured over time. Thus the method of the invention which combines sequential application of a mixable composition with a commercial mascara "wet on wet" provides superior benefits and properties.

Example 5

Further studies were conducted to demonstrate the benefits of wet on wet application of the mixable composition with the pigmented composition. The mixable composition of Example 1 was used. A pigmented oil in water emulsion lash composition was prepared as follows:

| Ingredient | % by weight |
|---|---|
| Water | QS100 |
| Iron oxides | 9.00 |
| Stearic acid | 5.50 |
| Bayberry wax | 4.85 |
| Sucrose polybehenate | 4.00 |
| Polyisobutene | 3.50 |
| Mica | 3.20 |
| Polyvinyl acetate | 3.15 |
| Paraffin | 3.00 |
| Aminomethyl propanediol | 1.60 |
| Isostearic acid | 1.20 |
| Kaolin | 1.00 |
| Phenoxyethanol | 1.00 |
| Silica | 0.80 |
| Hydroxyethylcellulose | 0.70 |
| Caprylyl glycol | 0.55 |
| Hydrogenated olive oil | 0.55 |
| Carnauba wax | 0.50 |
| PTFE | 0.50 |
| VP/Eicosene copolymer | 0.50 |
| Olive Fruit oil | 0.38 |
| Cholesterol | 0.10 |
| Hexylene glycol | 0.10 |
| Olive oil | 0.08 |
| Sodium polyacrylate | 0.72 |
| Rosemary extract | 0.05 |
| Nylon 6 | 0.05 |
| Polyaminopropyl biguanide | 0.5 |
| Black 2 | 0.04 |
| Simethicone | 0.04 |
| Polyester-5 | 0.03 |
| Panthenol | 0.03 |
| PVP | 0.02 |
| Pantethine | 0.02 |
| Preservatives | 0.05 |

The composition was prepared by combining the oil phase ingredients and the water phase ingredients and mixing well to emulsify. The resulting mascara composition was black in color and stored in a cylindrical container.

The Example 1 mixable composition and the pigmented lash composition of this Example 5 were tested as follows:

Test #1: The Example 1 composition, about 0.11 gram, was charged onto a twisted metal wire brush applicator and applied to lashes of one eye with 40 strokes; followed by recharging the applicator with about 0.11 gram of the Example 1 composition and application to lashes of second eye with 40 strokes. The mixable composition was allowed to dry on the lashes for 1 hour. Next, about 0.2 grams of the Example 5 mascara was charged onto a twisted metal wire brush applicator and applied to the lashes of one eye with 20 strokes. The applicator was recharged with about 0.2 grams of the Example 5 mascara and applied to the lashes of the second eye with 20 strokes. In both cases the Example 5 mascara composition dragged when stroked across the lashes; the composition was difficult to spread on the lashes and pulled the lashes; after application the mascara composition appeared clumpy and "crunchy", that is it appeared to contain chunks of product.

Test 2: Test 1 was repeated, except that in both cases the application of the mascara composition occurred immediately after application of the Example 1 composition and before the Example 1 composition had air dried. The Example 5 mascara composition applied to the undried Example 1 composition very smoothly with no tugging. The mixed compositions were smooth and homogeneous and provided good volume with a dramatic lash appearance, and no excess clumping.

Test 3: The application order of the Example 1 and Example 5 compositions was reversed. Specifically, about 0.5 grams of the Example 5 mascara composition was applied to the lashes of one eye using 20 strokes. The applicator was recharged with 0.5 grams of the Example 5 mascara and applied to the lashes of the second eye using 20 strokes. The Example 5 mascara was allowed to dry on the lashes for 1 hour. Then the Example 1 mixable composition was applied to the lashes. About 0.1 grams of the Example 1 composition was applied with the applicator with 40 strokes. The applicator was recharged with about 0.1 grams of the composition and applied to the second eye with 40 strokes. The Example 1 composition was difficult to apply over the dried mascara composition, drag was observed, and the composition did not spread well.

Test 4: The Example 1 and Example 5 compositions were applied as in Test 3 except that the Example 1 composition was applied immediately after the Example 5 composition and with the Example 5 composition not being completely dry. The resulting application was smooth, the products mixed well, and both films air dried to a homogeneous finish.

Test 5: Test 4, above was performed except that 40 strokes of both the Example 1 and Example 5 compositions were applied with no drying between application order of the Example 1 and Example 5 compositions. Although the compositions applied and mixed well to form a smooth homogeneous film that air dried well, 40 strokes of both compositions resulted in too much product being applied, leaving lashes overly coated with mascara and mixable composition.

In conclusion this test showed that when the mixable composition and the pigmented composition are applied sequentially, in either order, without allowing the compositions to air dry, and using 20 strokes of the mixable composition and 40 strokes of the pigmented composition, the end result is optimal. In particular, the coating applied to lashes is smooth, homogeneous, mixes well, and is compatible and when air dried provides a long wearing finish.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for coloring eyelashes comprising the steps of sequentially applying to the eyelashes a mixable water in oil emulsion composition comprising 1-30% water, 0.5-80% volatile solvent, 0.01-35% crosslinked silicone film former, 1-15% non-volatile oil, and 0.1-20% quaternized montmorillonite mineral; followed by a pigmented oil in water emulsion composition comprising 1-80% water, 0.1-25% film forming polymer, 0.1-20% oil and 0.1-20% pigments, wherein the mixable composition and the pigmented composition are applied sequentially wet on wet and upon application the mixable composition mixes and combines with the pigmented composition in the wet state to form a final mixed composition that upon air drying forms a homogeneous film, with all percentages by weight of the total compositions.

2. The method of claim 1 wherein from about 0.05 to 0.30 grams of mixable composition is applied to the lashes with an applicator that applies the mixable composition with 10-60 strokes of said applicator on the lashes.

3. The method of claim 2 wherein the mixable composition comprises a volatile solvent that is a mixture of paraffinic hydrocarbon and silicone; a crosslinked silicone film former that is a siloxane resin is selected from the group consisting of dimethicone silylate, trimethylsiloxysilicate, and mixtures thereof; the quaternized montmorillonite mineral is in the form of a dispersion with at least one volatile solvent; at least one non-volatile oil comprising one or more sorbitan esters; at least one wax; and water.

4. The method of claim 2 wherein the mixable composition is pigmented.

5. The method of claim 1 wherein from about 0.05 to 0.45 grams of the pigmented composition is applied from an applicator with 10-60 strokes of the applicator.

6. The method of claim 5 wherein the pigmented composition is applied sequentially to the lashes of one eye followed by the lashes of the second eye.

7. The method of claim 1 wherein from about 0.05 to 0.45 grams of the pigmented composition is applied to the lashes of one eye with 10-60 strokes of an applicator; the applicator is recharged with from about 0.05 to 0.45 grams of the pigmented composition which is then applied to the lashes of the second eye with 10-60 strokes.

8. The method of claim 1 wherein the mixable composition is applied to the lashes of the first eye with an applicator loaded with 0.05 to 0.45 grams of the mixable composition applied with 10-60 strokes; the applicator is recharged with about 0.05 to 0.45 grams of the mixable composition and the mixable composition is applied to the second eye with 10-60 strokes; the compositions mix upon application and dry to form a homogeneous film.

9. The method of claim 8 wherein the applicators used to apply the mixable composition and the pigmented composition are twisted metal wire brushes.

10. The method of claim 8 wherein the mixable composition dries in 20.1 to 40 minutes and the pigmented composition dries in 5 to 20 minutes.

* * * * *